United States Patent [19]

Katz et al.

[11] Patent Number: 4,605,927
[45] Date of Patent: Aug. 12, 1986

[54] INTRA-ORAL CONTROL UNIT AND SYSTEM

[75] Inventors: Philip Katz, Princeton Junction; Henry S. Brenman, Cinnaminson, both of N.J.; Henry Hamarman, Philadelphia; Harold Schwartz, King of Prussia, both of Pa.

[73] Assignee: Thomas Jefferson University, Philadelphia, Pa.

[21] Appl. No.: 526,699

[22] Filed: Aug. 26, 1983

[51] Int. Cl.[4] .................. H04Q 9/00; H04B 1/034; G08B 21/00
[52] U.S. Cl. ........................ 340/825.19; 340/407; 340/539; 455/100
[58] Field of Search ............... 340/825.19, 407, 539; 455/100, 128; 128/903; 381/70

[56] References Cited

U.S. PATENT DOCUMENTS 4,473,905 9/1984 Katz et al. ..................... 381/70
4,502,151 2/1985 Castle et al. ................... 381/70
4,550,427 10/1985 Katz et al. ..................... 381/70

OTHER PUBLICATIONS

Burnett, P. and Sutton, R. A.: "A Portable Electronic 'Calling Device' as an Aid to 'Weaning' Ventilator-Dependent Tetraplegic Patients from Intermittent Positive Pressure Ventilation", *Paraplegia*, 17:563–566, 1979.
Cloran, A. J.; Lotz, J. W.; Campbell, H. D.; Wiechers, D. O.; "Oral Telescoping Orthosis: An Aid to Functional Rehabilitation of Quadriplegic Patients" *J.A.D.A.*, vol. 100, pp. 876–879, Jun., 1980.
Efthimiou, M. A.; Gordon, W. A.; Sell, G. H.; and Stratford, C.: "Electronic Assistive Devices: Their Impact on the Quality of Life of High Level Quadriplegic Persons" *Arch. Phys. Med. Rehabil.*, vol. 62, pp. 131–134, Mar., 1981.
Garrison, J. H.; "Emergency Signaling for a Person with Quadriplegia and Extraordinary Respiratory Risk", *Arch. Phys. Med. Rehabil.*, vol. 63, pp. 180–181, Apr., 1982.
Green, R.: "The Current Status of and Future Considerations for Environmental Control Systems", *Bull. Prost. Res.*, pp. 310–325, 1974.
Guittet, J.; Kwee, H. H.; Quetin, N.; Yclon, J.: "The Spartacus Telethesis: Manipulator Control Studies", *Bull. Prosth. Res.*, BPR 10-32, pp. 69–105, Fall, 1979.
Jones, R. D.; Hooper, R. H.; Armstrong, D. I.; Fisher, C. J.; Tait, J.J.: "Microprocessor-based Multi-Patient Environmental-Control System for a Spinal Injuries Unit", *Med. & Biol. Eng. & Comput.*, 18:607–616, Sep., 1980.
Katz, P.; Schwartz, H. L.; Brenman, H. S. and Lowry, L. D.: "A Clinical Device for Revocalization of the Laryngectomized Patient", *IEEE Fron. Eng. Health Care*, pp. 318–320, Sep., 1981.

(List continued on next page.)

*Primary Examiner*—Donald J. Yusko
*Attorney, Agent, or Firm*—Woodcock Washburn Kurtz Mackiewicz & Norris

[57] ABSTRACT

A system for quadriplegics and for others having less than full use of their limbs for controlling the environment is disclosed. The system includes an intra-oral lingually operated switch located on a dental appliance. The switch activates an intra-oral power supply and intra-oral FM transmitter which directs control signals from the inside of the oral cavity to an external FM receiver. A controller responsive to the receiver generates output signals for operating call devices, and for controlling various appliances such as televisions, lights, bed position, etc. In one embodiment, a delay circuit is interposed between the intra-oral switch and the power supply such that inadvertent closure of the switch with the tongue does not cause undue power drain. An improved FM transmitter circuit is also disclosed which has low power drain, has low mass and temperature sensitivity and is not directional.

13 Claims, 4 Drawing Figures

Newhouse, V. L.; Ho, C. T.; and Pairitz, J. F.: "Voice Operated Transducer for the Disabled", *J. Clin. Eng.*, vol. 5, No. 2, Apr.–Jun., 1980, pp. 139–144.

Parish, J. G.: "A Study of the Use of Electronic Environmental Control Systems by Severely Paralysed Patients", *Paraplegia* 17, 147–152, 1979–1980.

Powner, D. J.: "Call Systems for Quadriplegic Patients", *Critical Care Medicine*, 312–313, Fall, 1980.

Schmeisser, G. and Seamone W.: "An Assistive Equipment Controller for Quadriplegics", *Johns Hopkins Med. Journ.*, 145:84–88, 1979.

Schwartz, H. L.; Westerhouse, J.; Zafran, J. and Zayon, G.: "A Study of Tongue Movements Using Dynamic Palatography", *Proc. 29th ACEMB*, 1976.

Schwartz, H. L. and Taylor, D. R.: "The Observation of Tongue Movements Using Dynamic Palatography", *Proc. 30th ACEMB*, 1977.

Schwartz, H. L. and Katz, P.: "Biofeedback Device for Tongue Placement Evaluation/Therapy", Proc. 33rd ACEMB, 1980.

Sell, G. H.; Stratford, D. C.; Zimmerman, M. E.; Youdin; Milner, D.: "Environmental and Typewriter Control Systems for High-Level Quadriplegic Patients: Evaluation and Prescription", *Arch. Phys. Med. Rehabil.*, 60:246–252, 1979.

Shannon, D. A.; Staewen, W. S.; Miller, J. T.; Cohen, B.S.: "Morse-Code-Controlled Computer Aid for the Nonvocal Quadriplegic", Med. Instr., vol. 15, No. 5, 341–343, Sep.–Oct., 1981.

Steadman, J. W.; Ferris, D. C.; and Rhodine, C. N.: "Prosthetic Communication Device", *Arch. Phys. Med. Rehabil.*, vol. 61, pp. 93–97, Feb., 1980.

Tunstall, M. E. and Bolton, M. P.: "Simple Alarm for Quadriplegic Patients", Anaesthesia, 1977, vol. 32, pp. 177–178.

Young, J. S. and Northup, N. E.: "Statistical Information Pertaining to Some of the Most Commonly Asked Questions about SCI", National Spinal Cord Injury Data Research Center, Phoenix, AZ, Aug., 1979.

Zimmerman, M. D.: "Technology for the Handicapped", Mach. Design, pp. 38–43, Apr., 1982.

Rinard, G.; Rugg, D.: "An Ocular Control Device for Use by the Severely Handicapped", *Conference System & Devices for Disabled*, Boston, Jun., 1976.

Rusk, H. A.: "Evaluation of Electronic Self-Help Devices for Severely Disabled Patients", *Bulletin of Prosthetics Research BPR 10–33*, vol. 17, No. 1, Spring, 1980.

Burnham, L. and Werner, G.: "The High-Level Tetraplegic; Phychological Survival and Adjustment", *Paraplegia 16*, 184–192, 1978–1979.

Warren, C. G.; Wilson, S. and Terami, B.: "Electric Bed Control: Mechanical Assist for Quadriplegic Patients", *Arch. Phys. Med. Rehabil.*, vol. 55, 560–561, 1974.

Peizer, E.; Lorenze, E. J. and Dixon, M.: "Environmental Controls to Promote Independence in Severely Disabled Elderly Persons", *Med. Instrumentation*, vol. 16, No. 3, May–Jun., 1982.

Rogers, J. C.; and Figone, J. J.: "Traumatic Quadriplegia: Follow-up Study of Self-Care Skills", *Arch. Phys. Med. Rehabil.*, vol. 61, pp. 316–321, Jul., 1980.

INTRA-ORAL CONTROL UNIT AND SYSTEM

BACKGROUND OF THE INVENTION

The present invention relates in general to an intra-oral control unit and system and, in particular it relates to an intra-oral control unit and system for use in controlling the environment of persons having less than full use of their limbs and which is especially useful for quadriplegics.

An increasing number of patients with high-level spinal cord injuries resulting in quadriplegia are being treated. The quadriplegic condition can result from many causes such as trauma which is due to vehicular and diving accidents, gunshot wounds, etc., spinal tumors or congenital malformations of the vertebrae, bacterial and viral infections, and neuromuscular disorders such as muscular dystrophy and multiple sclerosis. Many quadriplegic patients have a serious problem in communication during the early phase of their hospital stay. This problem with communication is a result of being ventilator-dependent, or of having minimal voice control. The treatment of the quadriplegic patient is first concerned with the survival of the patient and this usually occurs in an intensive care unit. At this stage of treatment, the patient has either significantly compromised respiratory parameters or is mute due to ventilator dependence. Many such patients have no mobility of the head due to traction. Many patients with cervical lesions remain in permanent traction for four to six weeks during which time the head is held in a position perpendicular to the surface of the bed. Because of this degree of restriction and the isolation in an intensive care unit, it is vital that the patient be provided with a device to gain the attention of the clinician.

Many types of patient-operated call systems have been used for such patients and are described in the literature. Such call devices may generally be categorized as sip/puff mechanisms, mouth wands and physiological response devices such as eye blink detectors and movement activated switches. All of these devices suffer from disadvantages associated with their use. The use of an air activated switch, such as a sip/puff device, is often not possible due to significantly compromised respiratory parameters or ventilator dependence. Even when sufficient air supply exists, the patient's speech may tend to be unreliable in volume and pronunciation. Thus, voice actuated devices are also unreliable. While the use of a mouth wand or stick is feasible, its communicative properties are slow and tiring to the user. Physiological response devices, such as eye blink detectors and movement activated switches tend to be unreliable. Physiological response devices falling into this category, in addition to eye blink detectors, include devices for the detection of head or shoulder motions, devices for the detection of myoelectric signals from the muscles around the head and neck, devices for the detection of eyebrow motion, jaw or chin movement and tongue contact. Utilization of such devices including those dependent upon residual arm, shoulder or leg movement of the patient for activation of physiological response devices is undesirable because such TJU-16 devices tend to produce inconsistent results and must be customized to each patient.

The present invention seeks to overcome the aforementioned disadvantages by providing a call device which capitalizes upon the fact that one voluntary function which is usually intact in a quadriplegic patient is the lingual function. Since the control of the tongue is vital for the primary acts of swallowing and eating, its capability is always evaluated early in the patient's treatment and reinforced if necessary. Devices for environmental control by a quadriplegic utilizing the tongue are known. One such system has been described for use by a quadriplegic which includes the placement of an electrical contact below the external lower lip which is activated by the tongue of a quadriplegic in order to sound an alarm. See M. E. Tunstall and M. P. Bolten, "Simple Alarm for Quadriplegic Patients", Vol. 32, *Anesthesia,* pages 177-178, 1977. Such a device suffers from severe disadvantages.

After the initial therapeutic phase in an intensive care unit, the quadriplegic patient has usually progressed to the point where in addition to the need for calling someone, it is desirable to control surrounding devices. Devices are known which control various pieces of equipment used by quadriplegics such as alarms, wheelchairs, computers, telephones and typewriters. In this category, devices are known which utilize head movements, sip/puff switches, vocal commands and finger or thumb movements for the activation of environmental control units. Such techniques suffer from the disadvantages referred to above.

It is an object of the present invention to provide an environmental control unit and system which obviates the aforementioned disadvantages.

It is a further object of the present invention to provide an environmental control unit and system which may be used as a call device and which alternatively may also be used to control external equipment and appliances.

It is a still further object of the present invention to provide such a unit and system which is activated by the tongue but which is mounted internally.

It is still another object of the present invention to provide an environmental control system capable of monitoring a plurality of quadriplegic patients simultaneously.

It is a still further object of the present invention to provide a system which is useful in any application in which an individual is required to control his external environment but is unable to use his limbs.

SUMMARY OF THE INVENTION

The foregoing objectives are achieved in accordance with the present invention by the provision of an environmental control unit which includes an intra-oral, lingually operated switching means, an intra-oral power supply and an intra-oral transmitter responsive to the switching means and to the power supply for transmitting control signals upon lingual activation of the switching means. In accordance with an important aspect of the present invention, the intra-oral transmitter comprises at least a first oscillating means for generating a first low frequency modulating signal only upon lingual activation of the switching means. A second oscillating means for generating a relatively high frequency carrier signal is provided, as is a means for frequency modulating the low frequency signal upon the carrier signal to produce a control signal for transmission.

In accordance with an important aspect of the present invention, the environmental control unit mentioned above is part of an overall environmental control system which includes an external FM receiver and a controller responsive to that receiver. The controller may be utilized to operate a call device in one embodiment. In still another embodiment of the present invention, the controller may be utilized to provide environmental control such as, for example, the operation of servo mechanisms to raise and lower a bed position, to increase or decrease room temperature, to change television volume, channel, etc.

In accordance with still another embodiment of the present invention, a plurality of patients are each provided with an environmental control unit which is monitored by a single FM receiver. The modulated signal transmitted from each patient differs from that of other patients and thus a plurality of patients may be monitored in a simple and efficient manner.

Intra-oral lingually operated switching means, of a type useful in the practice of the present invention, are known. One such switching means is disclosed in copending application Ser. No. 438,376 filed Nov. 1, 1982 by Philip Katz, Henry S. Brenman, Louis D. Lowry and Harold Schwartz entitled "Artificial Larynx", which application is incorporated herein by reference. In that application, an intra-oral switching means is disclosed which is placed upon a dental appliance, the switching means being closed when the tongue bridges electrical contacts on the appliance. In copending application Ser. No. 438,376, however, the output of the device disclosed therein is acoustic rather than electromagnetic. While the intra-oral cavity is a satisfactory environment from which to transmit acoustic energy, this cavity represents a severely hostile environment from which to transmit electromagnetic energy of the type envisioned in the present application.

Transmission of electrical energy from the intra-oral cavity imposes severe design constraints upon the realization of both the transmitter and power supply of the present invention. First, the intra-oral cavity represents only a small volume in which to house the components required for the present invention. Second, the absorbance of the surrounding tissue of the intra-oral cavity makes signal transmission from it a difficult task. Thirdly, the temperature of an intra-oral transmitter may vary substantially from that of body temperature depending upon the temperature of the air passing through the cavity. Since the carrier frequency of the transmitter oscillator is often temperature-dependent many transmitter oscillator designs are simply inapplicable. Because of these constraints, an intra-oral transmitter of the present invention must be small in size and have low power consumption. It must also be one which is not directional such that movement of the transmitter with respect to the receiver causes a diminution in signal. Still further, it must be one which is not temperature dependent and which is not mass sensitive, i.e., does not suffer a degradation in signal upon movement of the patient's tongue.

In the development of the intra-oral transmitter of the present invention and in an attempt to avoid these constraints various approaches were tried. Amplitude modulation, as opposed to frequency modulation, was first employed. It was found that intra-oral transmitters employing amplitude modulation were directional, had low sensitivity, and high power drain. It was also found that such transmitters had a size which is unduly large.

Tunnel diode transmitters, both FM and AM were next employed. It was found that such transmitters did not have suitable frequency stability. FM transmitters were also tried having LC oscillator circuits of the Colpitts type and also of the Hartley type. It was found that these transmitters had high power consumption and were both mass and temperature sensitive. Attempts were also made employing transmitters having crystal oscillators. It was found that such transmitters were unduly large, were mass sensitive and were difficult to tune. Designs employing crystal controlled varacter transmitters were also attempted, but it was found that these, too, were unduly large and had excessive power drain. Finally, an FM transmitter which employs a modified Colpitts oscillator was designed and employed which was suitable for reliable transmission from the intra-oral cavity.

Thus, in addition to a general concept set forth above, the present invention is also directed to a specific intra-oral FM transmitter which does not suffer from the aforementioned adverse temperature dependence, mass sensitivity, and directionality, which is sufficiently miniaturized so as to be located intra-orally and which has sufficiently low power drain as to permit use over extended periods of time and which is suitably sealed to function in the hostile environment.

BRIEF DESCRIPTION OF THE DRAWINGS

The present invention will be more fully understood by reference to the accompanying drawings in which.

DETAILED DESCRIPTION OF THE PREFERRED EMBODIMENT

Figure 1:
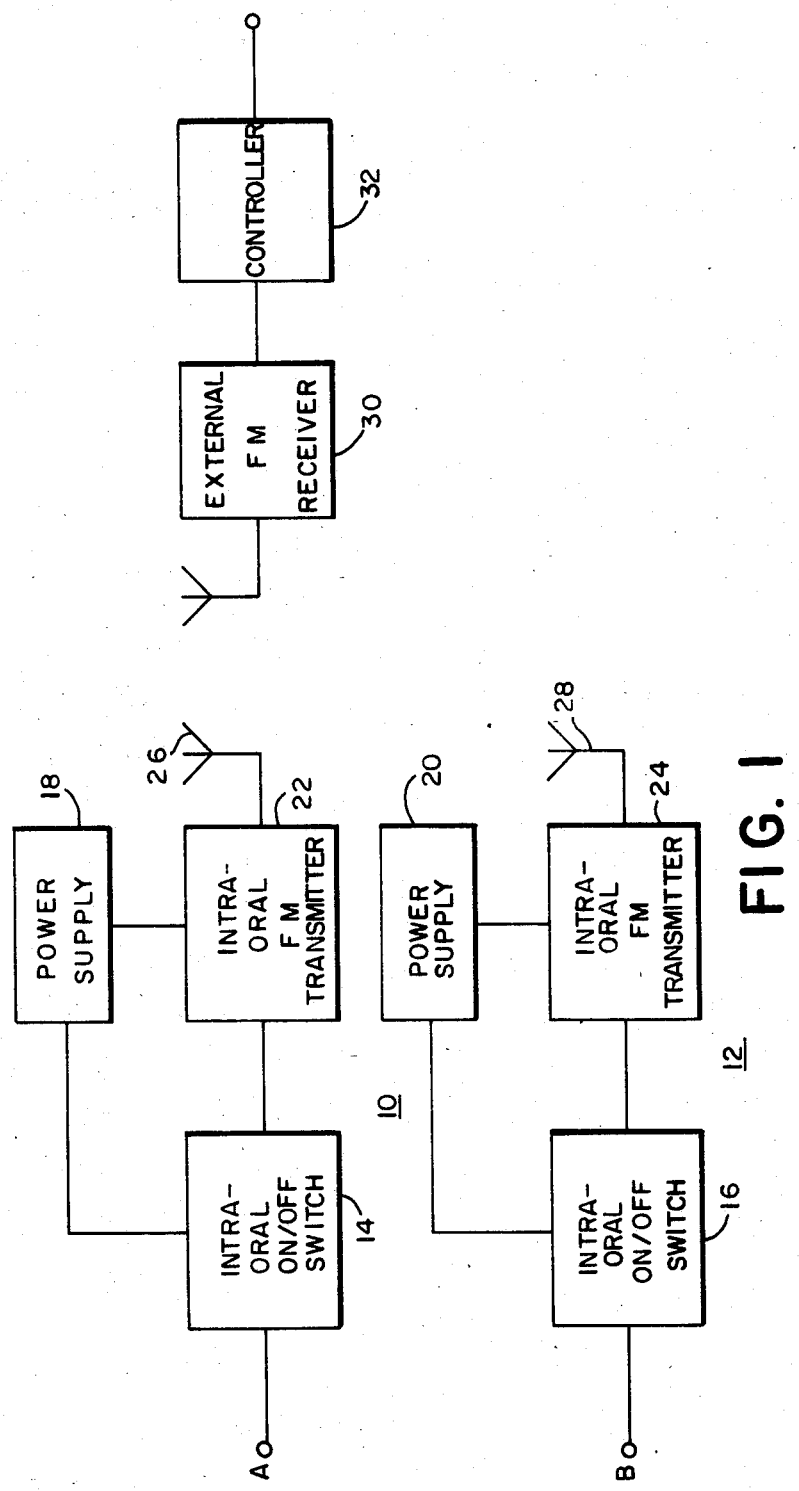
FIG. 1 is a block diagram of an environmental control system of the present invention.

Referring now to FIG. 1 a block diagram of the environmental control unit and system of the present invention is disclosed. In the embodiment shown in FIG. 1, two environmental control units 10 and 12 are shown, the unit 10 being used by a first patient A and the unit 12 being utilized by a second patient B.

Each of the environmental control units 10 and 12 employs an intra-oral on/off switching means 14 and 16, res-pectively. The intra-oral on/off switching means 14 and 16 are of a type disclosed in copending application Ser. No. 438,376 filed Nov. 1, 1982 mentioned above which is incorporated herein by reference.

Each of the environmental control units 10 and 12 also includes an on-board power supply 18 and 20, respectively. In accordance with the preferred embodiment of the present invention this power supply comprises batteries which may be of the lithium, silver oxide or nickel cadmium type, although 3 volt lithium batteries are particularly preferred. The intra-oral switching means 14 and 16 are preferably located on a conventional palatal denture or dental appliance. The body of the dental appliance is formed from conventional dental prosthetic materials, such as an acrylic polymer, which is shaped to fit comfortably against the roof of the wearer's mouth. Located upon this prosthesis are contacts which are lingually activated. The contacts are preferably one or more pairs of Ag-AgCl contacts which may be bridged with the tongue or alternatively a sealed momentary switch which may be activated by the tongue. In the case of the Ag-AgCl contacts, the touching of such contacts by the tongue completes a ground path for activating an intra-oral FM transmitter 22, 24 located in each environmental control unit 10, 12. The output of the FM transmitter 22, 24 is connected to an antenna means 26, 28 from which emanates control signals for transmission outside the intra-oral cavity. Each FM transmitter 22, 24 employs the same carrier frequency, but with each having its own unique subcarrier frequency. The environmental control unit 10 is encapsulated with a suitable sealant such as medical grade silicone-type adhesive.

Each of the intra-oral environmental control units 10 and 12 referred to above are part of a single overall environmental control system for use with a plurality of patients. In addition to the intra-oral control units 10 and 12, this system includes an external FM receiver 30 which monitors a plurality of patients and an external controller 32. The FM receiver 30 is tuned to receive FM carrier signals emanating from antennae 26, 28. This external FM receiver operates in the FM band (88 to 108 MHz).

The audio output of the FM receiver 30 is directed to the controller 32 which includes a plurality of phase-lock loop tone decoders each associated with the subcarrier frequency of the monitored patient. The output of the phase-lock loop tone decoders of controller 32 may be used to control a simple device such as a latching relay or lamp to summon a nurse, a stepper mechanism to change television channels, or a more sophisticated sequencer to control a remote control device.

Figure 2:
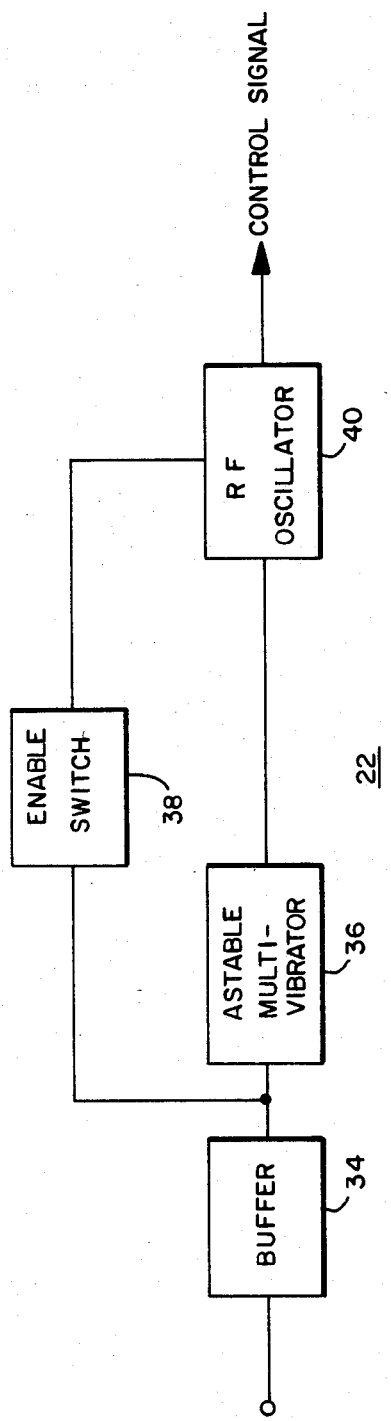
FIG. 2 is a block diagram of an intra-oral transmitter of the type useful in connection with the system of FIG. 1.

Referring now to FIG. 2 a detailed block diagram of one intra-oral FM transmitter 22 is shown, it being understood that other such transmitters are similar. The transmitter 22 may include an input buffer 34, the input to which is connected to the intra-oral switching means 14. The output of the buffer 34 is connected to a first oscillating means 36 for generating a first low frequency modulating signal only upon lingual activation of the switching means 14. This oscillating means 36 preferably comprises an astable multivibrator of the type which will be more fully described below. The output of buffer 34 is also preferably connected to an enable switch 38, the output of which is directed to a second oscillating means or circuit 40. The second oscillating circuit 40 is also responsive to the astable multivibrator 36. The oscillating circuit 40 generates a high frequency carrier signal and also modulates the low frequency signal emanating from the astable multivibrator 36 upon that carrier signal so as to produce a first control signal for transmission.

Figure 3:
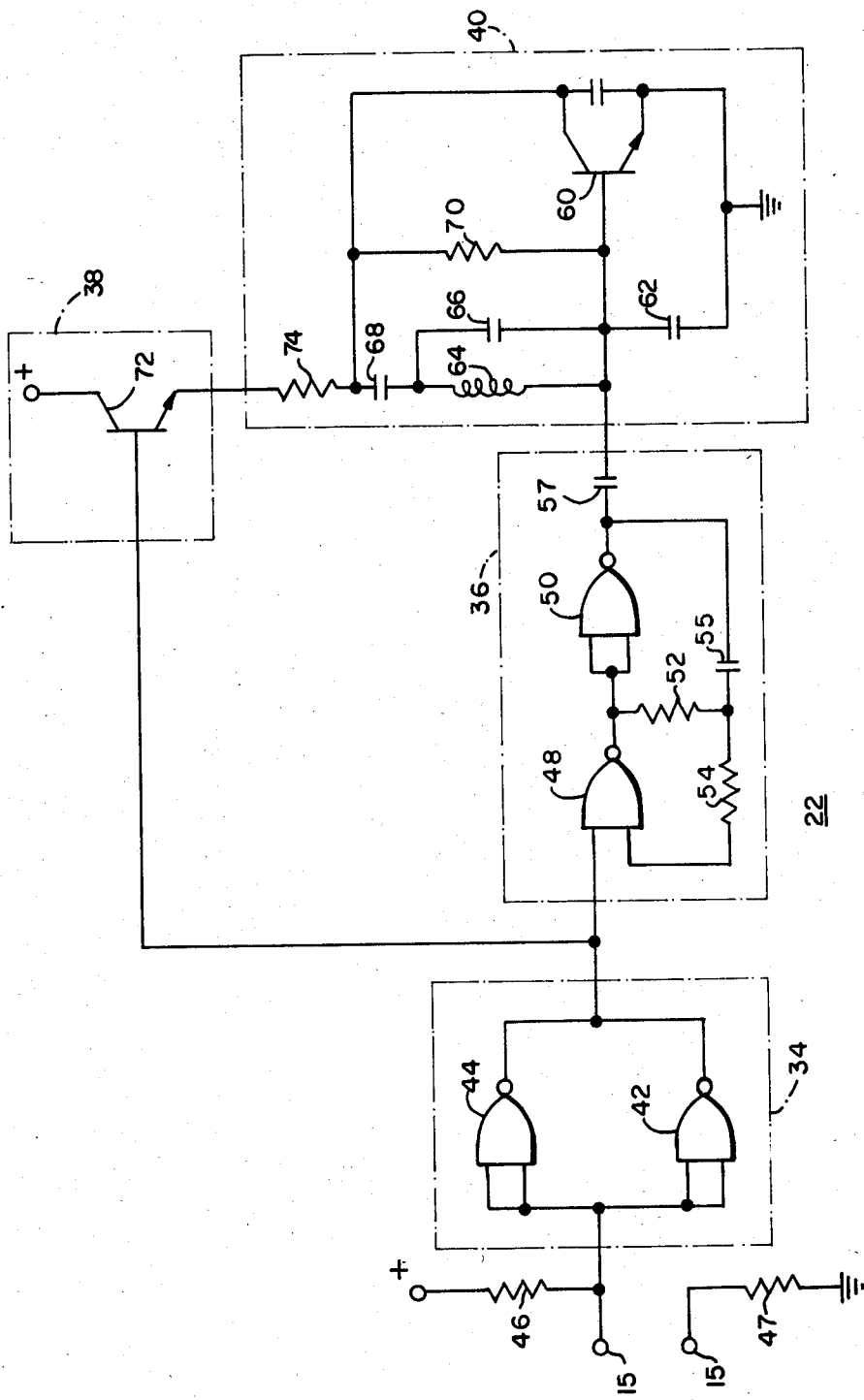
FIG. 3 is a schematic circuit diagram of an intra-oral transmitter which is appropriate for the practice of the present invention.

Referring now to FIG. 3 a detailed circuit diagram of the intra-oral FM transmitter 22 shown in FIG. 2 will be described. As shown, the input buffer 34 preferably comprises a pair of parallel connected NAND gates 42 and 44. The inputs to NAND gates 42 and 44 are connected via resistor 46 to a source of positive voltage at power supply 18. When the contacts 15 of the intra-oral switch 14 are closed the inputs to the NAND gates 42 and 44 are also connected to ground through a resistor 47. The outputs of NAND gates 42 and 44 are directed to the astable multivibrator 36 as shown. The contacts 15 of the intra-oral switching means 14 are such that the input to NAND gates 42 and 44 goes low upon lingual activation of the switching means 14. The output of the buffer 34 thus provides a conditioned signal for activation of the astable multivibrator 36.

The first oscillating means or astable multivibrator 36 preferably comprises NAND gates 48 and 50, one input to NAND gate 48 being the output from buffer 34. The output of NAND gate 48 is directed back to the remaining input of that gate through resistors 52, 54 as shown. The output of NAND gate 48 is also directed to both inputs of NAND gate 50 with feedback being provided from the output thereof through capacitor 55 and resistor 52. The output of NAND gate 50 is connected via capacitor 57 to the second oscillating circuit 40. Thus, the output of astable multivibrator 36 comprises a low frequency modulating signal generated only upon lingual activation of the switching means 14, the signal preferably having a frequency of approximately 1 KHz. This low frequency modulating signal is directed to the second oscillating circuit 40 as shown.

While not shown in FIG. 3, it is within the scope of the present invention to provide more than a single oscillating means 36, each such oscillating means generating low frequency modulating signals of slightly differing frequency. In an embodiment in which more than a single oscillating means 36 is provided, intra-oral switching means having more than a single pair of intra-oral contacts are also provided such that the patient, by closing the appropriate set of contacts may select a particular low frequency modulating signal from one or the other oscillating means 36 so as to provide modulating signals which can generate differing control signals. For example, selection of a modulating signal of a first frequency may be utilized so as to emit a first control signal indicating a call for assistance whereas the emanation of a second control signal of varying duration may be utilized to raise or lower a bed position, change television channels, etc.

The second oscillating circuit 40 in accordance with an important aspect of the present invention is a modified Colpitts type oscillating circuit. This circuit generates a relatively high frequency carrier signal, for example, 88 MHz. This second oscillating circuit 40 preferably comprises a transistor 60, the emitter of which is connected to ground and the base of which is also connected to ground via a capacitor 62. The collector-base circuit of the transistor 60 includes an LC network comprising inductor 64 in parallel with capacitor 66. This LC network in series with capacitor 68 is connected between the collector and base of transistor 60. Also connected between the collector and base is resistor 70 which completes the collector-base network. The oscillating circuit 40 is enabled by virtue of enable switch 38 which comprises a transistor 72, the collector of which is connected to a source of positive voltage at the on-board power supply. The base of transistor 72 is connected to the output of buffer 34 while the emitter is connected via resistor 74 to the collector-base network of the transistor 60. The enable switch 38 permits activation of the second oscillating circuit 40 only when the intra-oral switching means 14 is lingually activated. On other occasions, the second oscillating circuit 40 is dormant so as to preclude power drain.

The circuit shown in FIG. 3 is particularly advantageous for use in accordance with the present invention for the reason that it generates a highly stable carrier frequency which is not dependent upon temperature, which is not directional and which is not mass sensitive. Moreover, the circuit shown in FIG. 3 has low power drain and is sufficiently miniaturized so as to permit intra-oral mounting of the same. While the circuit shown in FIG. 3 is particularly useful in the practice of the present invention, a further improved transmitter circuit has been developed and is shown in FIG. 4.

Figure 4:
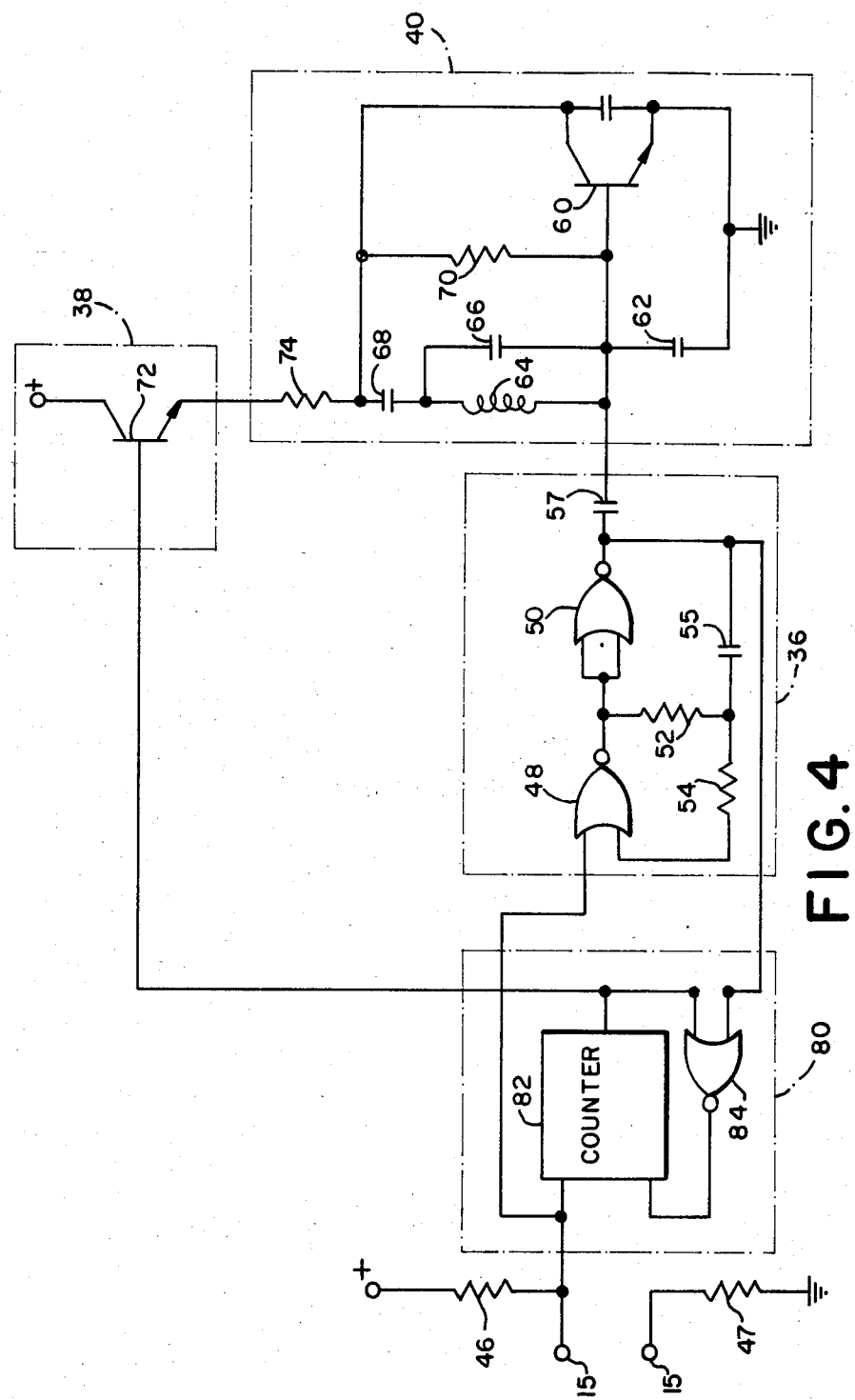
FIG. 4 is a schematic circuit diagram illustrating an improved embodiment of an intra-oral transmitter which is particularly useful in the environmental control system of the present invention.

The circuit shown in FIG. 4 is in all respects the same as the circuit shown in FIG. 3 insofar as both circuits employ the same oscillating circuit 40, the same enable switch 38 and the same astable multivibrator circuit 36. The circuit of FIG. 4, differs from the circuit of FIG. 3 in the logic used, i.e., NAND type in FIG. 3 and NOR type in FIG. 4, and also insofar as it includes a time delay circuit 80 in lieu of a buffer 34. The time delay circuit 80 includes a counter 82 the reset input of which is connected to a source of positive voltage through resistor 46. The counter 82 is enabled when the contacts 15 of the intra-oral switch 14 are closed. The time delay circuit 80 further includes a NOR gate 84, one input of which is received from the output of astable multivibrator 36 while the other input of which is connected to the base of transistor 72 at the enable switch 38 and to the output of counter 82. The output of NOR gate 84 is also directed to the clock input of the counter 82. The output of counter 82, in addition to being directed to NOR gate 84 is also directed to the base of transistor 72.

In operation, the circuit of FIG. 4 prevents unwanted power drain by ensuring that inadvertent touching of the contacts 15 by the tongue does not automatically activate the intra-oral transmitter 40. Upon closing of the contacts 15 with the tongue the astable multivibrator 36 begins to oscillate. The oscillating signal from the multivibrator 36 is gated through NOR gate 84 to the counter 82. After a predetermined number of oscillations and therefore after a predetermined time delay the output of the counter 82 goes high thereby activating the enable switch 38 causing it, in turn, to activate the high-frequency oscillating circuit 40. When the tongue is removed from the contacts 15, the counter 82 is reset. Thus, the circuit of FIG. 4 enjoys all the benficial attributes of the circuit shown in FIG. 3 but further enjoys even lower power drain.

While a particular embodiment of the present invention has been shown and described, it will be appreciated that other embodiments are within the scope of the present invention as defined by the claims herein.

For example, while the present invention has been described in connection with environmental control for quadriplegics it also finds utility for other patients such as paraplegics, or others with neuromuscular dysfunctions. Moreover, the present invention may have utility in the provision of other control functions for anyone whose hands are either constrained or occupied.

What is claimed is:

1. An environmental control unit for transmitting control signals from patients to at least one external device comprising:
    at least one intra-oral lingually operated switching means;
    an intra-oral power supply; and
    an intra-oral transmitter responsive to said switching means and to said power supply for transmitting radio frequency control signals from an intra-oral cavity to a position external to said patients upon lingual activation of said switching means.

2. The environmental control unit of claim 1 in which said transmitter comprises:
    a first oscillating means for generating a first low frequency modulating signal only upon lingual activation of said switching means; and
    a second oscillating means for generating a relatively high frequency carrier signal and for frequency modulating said first low frequency signal upon said carrier signal to produce a first control signal.

3. The environmental control unit of claim 2 wherein said transmitter further comprises:
    a means responsive to said switching means for enabling said second oscillating means only upon lingual activation of said switching means.

4. The environmental control unit of claim 2 wherein said first oscillating means comprises:
    an astable multivibrator.

5. The environmental control unit of claim 4 wherein said intra-oral transmitter further comprises:
    a buffer connected between said switching means and said astable multivibrator.

6. The environmental control unit of claim 2 in which said intra-oral lingually operated switching means comprises a plurality of contacts and in which said transmitter further comprises:
    a third oscillating means for generating a second low frequency modulating signal different from said first, said second oscillating means being responsive to said first or to said third oscillating means to produce said control signals, a different control signal being transmitted depending upon which of said plurality of contacts is lingually activated.

7. The environmental control unit of claim 1 further comprising:
    a delay means responsive to said switching means, said power supply being responsive to said delay means whereby said intra-oral transmitter is enabled to transmit control signals only after a predetermined time delay.

8. An environmental control system adapted for use by a plurality of quadriplegic patients comprising:
    an environmental control unit for each patient in said plurality, each said unit including:
    at least one intra-oral lingually operated switching means;
    an intra-oral power supply;
    an intra-oral transmitter responsive to said switching means and to said power supply for transmitting radio frequency control signals uniquely identifying a particular one of said plurality of patients upon lingual activation of said switching means by that patient;
    an external receiver responsive to the control signals emitted by each intra-oral transmitter; and
    a controller responsive to said receiver for generating output signals for each patient in said group.

9. The environmental control system of claim 8 in which for each environmental control unit said intra-oral transmitter comprises:
    a first oscillating means for generating a first low frequency modulating signal only upon lingual activation of said switching means; and
    a second oscillating means for generating a relatively high frequency carrier signal and for frequency modulating said first low frequency signal upon said carrier signal to produce a first control signal.

10. The environmental control system of claim 9 in which each intra-oral lingually operated switching means comprises a plurality of contacts and in which each transmitter further comprises:
    a third oscillating means for generating a second low frequency modulating signal different from said first, said second oscillating means being responsive to said first or to said third oscillating means to produce said control signals, a different control signal being transmitted depending upon which of said plurality of contacts is lingually activated by that patient.

11. An environmental control system adapted for use by a quadriplegic patient comprising:
   an environmental control unit having at least one intra-oral lingually operated switching means;
   an intra-oral power supply;
   an intra-oral transmitter responsive to said switching means and to said power supply for transmitting radio frequency control signals upon lingual activation of said switching means;
   an external receiver responsive to said control signals emitted by said intra-oral transmitter; and
   a controller responsive to said receiver for generating output signals.

12. The environmental control system of claim 11 further comprising:
   a visual display responsive to said output signals.

13. The environmental control system of claim 11 further comprising:
   an audible signal responsive to said output signals.

* * * * *